United States Patent
Beach et al.

[11] Patent Number: 6,127,600
[45] Date of Patent: Oct. 3, 2000

[54] METHODS OF INCREASING ACCUMULATION OF ESSENTIAL AMINO ACIDS IN SEEDS

[75] Inventors: Larry Beach, Des Moines; Mitchell C. Tarczynski, West Des Moines, both of Iowa

[73] Assignee: Pioneer Hi-Bred International, Inc., Des Moines, Iowa

[21] Appl. No.: 08/826,341

[22] Filed: Mar. 26, 1997

Related U.S. Application Data

[63] Continuation of application No. 08/455,358, May 31, 1995, abandoned.

[51] Int. Cl.[7] .......................... C12N 15/00; C12N 15/29; C12N 15/82; A01H 4/00
[52] U.S. Cl. .......................... 800/278; 800/298; 435/419; 435/468; 435/320.1; 435/69.1; 536/24.1; 536/23.6
[58] Field of Search ........................ 800/205, 298, 800/278; 435/69.1, 172.3, 320.1, 419, 468; 536/24.1, 23.6

[56] References Cited

FOREIGN PATENT DOCUMENTS

| WO 93/19190 | 9/1993 | WIPO | C12N 15/82 |
|---|---|---|---|
| WO 94/20628 | 9/1994 | WIPO | C12N 15/82 |
| WO 95/15392 | 6/1995 | WIPO | C12N 15/82 |
| WO 95/31554 | 11/1995 | WIPO | C12N 15/60 |

OTHER PUBLICATIONS

Smith et al. Nature. vol. 334, pp. 724–726, Aug. 1988.
Napoli et al. The Plant Cell. vol. 2, pp. 279–289, Apr. 1990.
Karchi et al. The Plant Journal. vol. 3, No. 5, pp. 721–727, 1993.
Altenbach et al. Plant Molecular Biology. vol. 13, pp. 513–522, 1989.
Altenbach et al., "Manipulation of methionine–rich protein genes in plant seeds", *Trends in Biotechnology*, vol. 8, No. 6, pp. 156–160 (1990).

*Primary Examiner*—Lynette F. Smith
*Assistant Examiner*—Thomas Haas
*Attorney, Agent, or Firm*—Pioneer Hi-Bred International, Inc.

[57] ABSTRACT

The present invention provides a method for increasing the levels of essential amino acids in seeds of plants, thereby enhancing the nutritional value of the seeds. The method comprises manipulating the metabolic pathway of the amino acid to provide an increased source of the target free amino acid and, concomitantly, over-expressing a preselected gene coding for the protein containing the target amino acid, such that there is accumulation of protein-bound target amino acid. A complementary protein sink is thus produced. The present invention is particularly useful in increasing levels of methionine, lysine and threonine in seeds.

32 Claims, 1 Drawing Sheet

METHODS OF INCREASING ACCUMULATION OF ESSENTIAL AMINO ACIDS IN SEEDS

This application is a continuation of application Ser. No. 08/455,358 filed May 31, 1995, now abandoned.

FIELD OF THE INVENTION

The present invention relates to the field of animal nutrition. Specifically, the present invention related to methods of enhancing the nutritional content of seeds used as feed.

BACKGROUND

Feed formulations are required to provide animals essential nutrients critical to growth. However, crop plants are generally rendered food sources of poor nutritional quality because they contain low proportions of several amino acids which are essential for, but cannot be synthesized by, monogastric animals.

For many years researchers have attempted to improve the balance of essential amino acids in the seed proteins of important crops through breeding programs. As more becomes known about seed storage proteins and the expression of the genes which encode these proteins, and as transformation systems are developed for a greater variety of plants, molecular approaches for improving the nutritional quality of seed proteins can provide alternatives to the more conventional approaches. Thus, specific amino acid levels can be enhanced in a given crop via biotechnology.

One alternative method is to express a heterologous protein of favorable amino acid composition at levels sufficient to obviate feed supplementation. For example, a number of seed proteins rich in sulfur amino acids have been identified. A key to good expression of such proteins involves efficient expression cassettes with seed specific promoters. Not only must the gene-controlling regions direct the synthesis of high levels of mRNA, the mRNA must be translated into stable protein.

Among the essential amino acids needed for animal nutrition, often limiting from crop plants, are methionine, threonine and lysine. Attempts to increase the levels of these free amino acids by breeding, mutant selection and/or changing the composition of the storage proteins accumulated in crop plants has met with minimal success. Usually, the expression of the transgenic storage protein did not result in sufficient increase in the total seed amino acid. The phaseolin-promoted Brazil nut 2S expression cassette is an example of an effective chimeric seed-specific gene. However, even though Brazil nut protein increases the amount of total methionine and bound methionine, thereby improving nutritional value, there appears to be a threshold limitation as to the total amount of methionine that is accumulated in the seeds. The seeds remain insufficient as sources of methionine and methionine supplementation is required in diets utilizing the above soybeans.

An alternative to the enhancement of specific amino acid levels by altering the levels of proteins containing the desired amino acid is modification of amino acid biosynthesis. Recombinant DNA and gene transfer technologies have been applied to alter enzyme activity catalyzing key steps in the amino acid biosynthetic pathway. Glassman, U.S. Pat. No. 5,258,300; Galili, et al., European Patent Application No. 485970; (1992); incorporated herein in its entirety. However, modification of the amino acid levels in seeds is not always correlated with changes in the level of proteins that incorporate those amino acids. Burrow, et al., *Mol. Gen. Genet.*; Vol. 241; pp. 431–439; (1993); incorporated herein in its entirety by reference. Increases in free lysine levels in leaves and seeds have been obtained by selection for DHDPS mutants or by expressing the *E. coli* DHDPS in plants. However, since the level of free amino acids in seeds, in general, is only a minor fraction of the total amino acid content, these increases have been insufficient to significantly increase the total amino acid content of seed.

The lysC gene is a mutant bacterial aspartate kinase which is desensitized to feedback inhibition by lysine and threonine. Expression of this gene results in an increase in the level of methionine and threonine biosynthesis. However, expression of this gene with seed-specific expression cassettes has resulted in only a 6–7% increase in the level of total threonine or methionine in the seed. See Karchi, et al., *The Plant J.*; Vol. 3; pp. 721–7; (1993); incorporated herein in its entirety by reference. Thus, there is minimal impact on the nutritional value of seeds, and supplementation with essential amino acids is still required.

Based on the foregoing, there exists a need for methods of increasing the levels of essential amino acids in seeds of plants. As can be seen from the prior art, previous approaches have led to insufficient increases in the levels of both free and bound amino acids to significantly enhance the nutritional content of the feed. There exists a need to increase the levels of the essential amino acids by 100%, doubling existent levels. If this is achieved, supplementation will no longer be necessary.

It is therefore an object of the present invention to provide methods for genetically modifying seeds of plants to increase the levels of the essential amino acids threonine, methionine and lysine in the seeds of such plants.

It is a further object of the present invention to provide seeds for food and/or feed with higher levels of the essential amino acids, threonine, methionine and lysine, than wild type species of the same seeds.

It is a further object of the present invention to provide seeds for food and/or feed such that the level of the essential amino acids is doubled, thus obviating the need for feed supplementation.

SUMMARY

The present invention provides methods for genetically modifying seeds of plants to increase the levels of the essential amino acids threonine, methionine and lysine. The present methods involve a combination of providing an increased source of a target free amino acid population with a concomitantly produced, complementary protein sink, the result of which is an unexpectedly increased accumulation of protein-bound, target amino acid. The methods include 1) manipulation of the metabolic pathways of amino acids in seeds to provide an increase in the level and/or availability of essential amino acids such as threonine, methionine and/or lysine; and 2) the over-expression of preselected genes, either endogenous or heterologous, coding for seed proteins that contain essential amino acids such as threonine, methionine and/or lysine. Synthesis of sufficient free target amino acid as a source for incorporation into the concomitantly synthesized selected protein which acts as a sink eliminates the need for essential amino acid supplementation in feed.

DETAILED DESCRIPTION OF THE INVENTION

Figure 1:
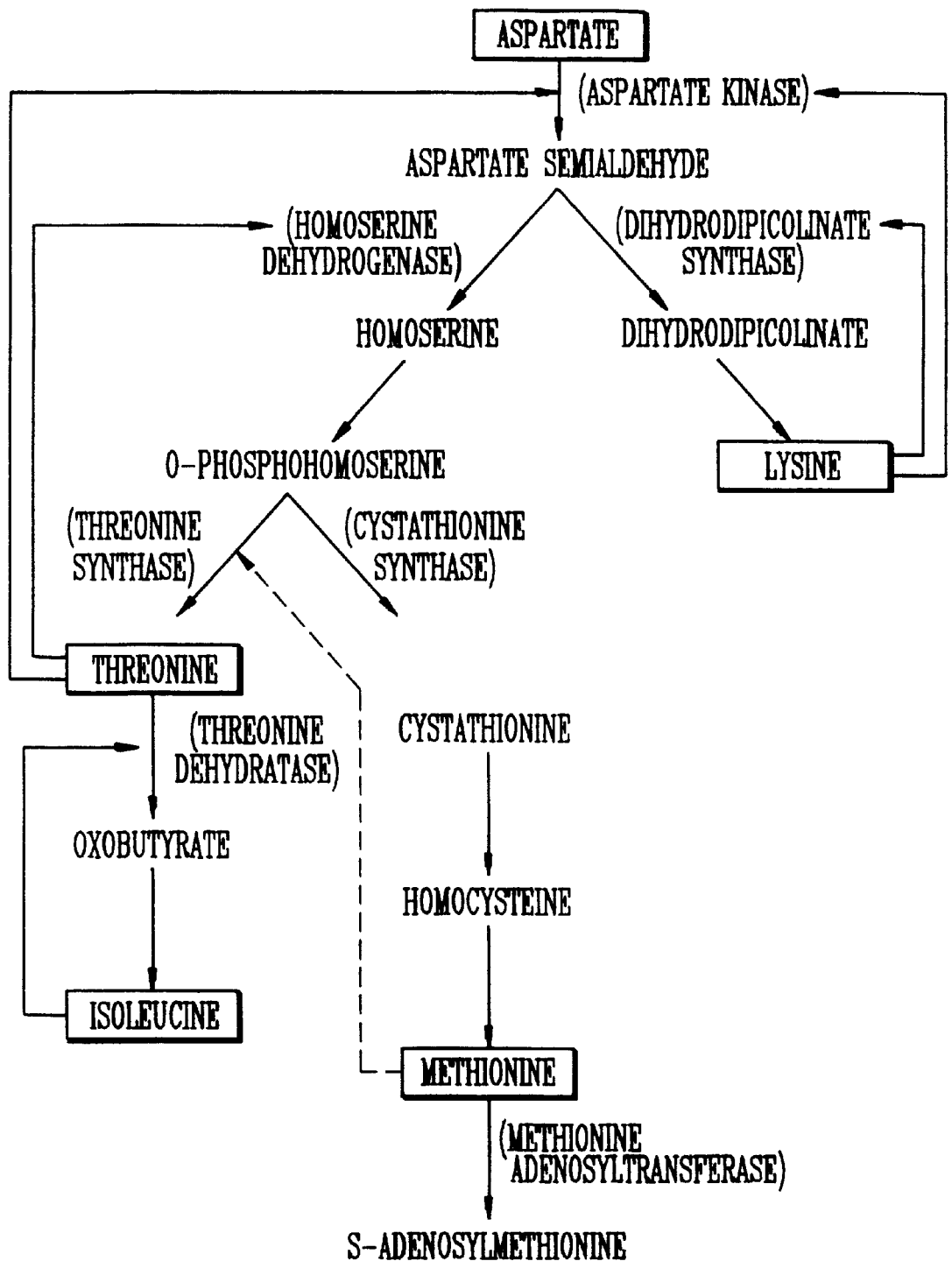
FIG. 1 depicts a diagram of the aspartate-family biosynthetic pathway.

As used herein, "sink" means a stably accumulated protein that may contain abundant amounts of targeted amino acid.

As used herein, "source" means free amino acids available for protein biosynthesis. These are synthesized de novo via biosynthetic pathways.

As used herein, "free amino acid" means amino acids that are unmodified or are the direct result of their synthesis.

As used herein, "bound amino acid" means amino acids that are modified, for example incorporated in peptides and proteins.

As used herein, "target amino acid" means an amino acid that is to be overproduced.

As used herein, "selected protein" means a protein, or its genetic equivalent, that contains elevated levels of target amino acid.

As used herein, "genetically modified" means a plant cell stably incorporating a nucleic acid construct introduced by transformation methods. The term "wild type" refers to an untransformed plant cell. "Endogenous" protein refers to the native protein normally found in its natural location in the plant.

In addition, the invention comprises the methods of preparing and using the various DNA constructs of the present invention. Plants, seeds and microorganisms transformed with the nucleic acid sequences described are also embodiments of the invention.

Preferred plants that produce seeds wherein protein content may be improved by this method include, but are not limited to soybeans, canola, corn, sunflower, wheat, barley, oats, millet, rice, sorghum, and rye. The seeds may be used directly as feed or food, or further processing may occur. In the practice of the present invention, the most preferred plant seed is *Glycine max*.

In accordance with this invention, there is provided simple, rapid, and reliable process for the production of transgenic soybean plants with increased accumulation of essential amino acids in the resulting seeds. The method is genotype independent and shows a substantial, unexpected improvement over previously used systems.

Manipulation of the Metabolic Pathways of Amino Acids

Recent advances in recombinant DNA and gene transfer technologies make it possible to isolate, sequence, manipulate and re-introduce genes into organisms. See e.g. Plant Biotechnology: Commercial Prospects and Problems, (1993), eds Prakash et el., Oxford & IBH Publishing Co., New Delhi, India; Molecular Biology and Genetic Engineering of Yeasts, (1992), Heslot, et al., CRC Press, Inc., USA; and Molecular Cloning: A Laboratory Manual, (1989), Sambrook, et al., Cold Spring Harbor Laboratory Press, Cold Spring Harbor, N.Y.; all incorporated herein in their entirety by reference. Use of these technologies permit the genetic manipulation of metabolic pathways, ultimately leading to changes in the concentrations of certain metabolites. See Bailey, et al., "Toward a Science of Metabolic Engineering," *Science*; Vol. 252; pp. 1668–1675; (1991); Muller-Rober, et al., "Inhibition of the ADP-glucose Pyrophosphorylase in Transgenic Potatoes Leads to Sugar-storing Tubers and Influences Tuber Formation and Expression of Tuber Storage Protein Genes." *The EMBO Journal*; Vol. 11(4); pp. 1229–1238; (1992); Sonnenwald, et al., "Transgenic Tobacco Plants Expressing Yeast-derived Invertase in either the Cytosol, Vacuole or Apoplast: a Powerful Tool for Studying Sucrose Metabolism and Sink/source Interactions," *The Plant Journal*, Vol. 1(1), pp. 95–106; (1991); and Tarczynski, et al., "Expression of Bacterial mtlD Gene in Transgenic Tobacco Leads to Production and Accumulation of Mannitol," *Proc. Natl. Acad. Sci.*, Vol. 89, pp. 2600–2604; (1992); all incorporated herein in their entirety by reference. Standard molecular approaches by which the metabolic pathways for the metabolism of threonine, methionine and lysine in seeds of plants can be altered are described hereinafter. The intent of these nonlimiting approaches is to increase supplies of these essential amino acids.

Over-expression of a Gene Coding for a Target Enzyme

This approach increases the concentration of a desired target enzyme which is a rate-limiting enzyme, usually regulated and at a metabolic branchpoint. See e.g. Van Schaewen, A., et al., *EMBO J.*; Vol. 9; pp. 3033–3044; (1990); and Dickinson, C. D., et al., *Plant Physiol.*; Vol. 95; pp. 420–425; (1991) both incorporated herein in their entirety by reference. Increased expression of the gene coding for the target enzyme can be achieved, for example, by increasing the strength of the promoter used to drive transcription of the gene and/or increasing the number of copies of the gene and its regulatory elements. Strong gene expression and multiple copies of the gene lead to increased levels of mRNA and target enzyme. The increase in the concentration of the target enzyme increases metabolic flow through the rate-limiting step.

For example, an increase in cystathionine gamma-synthase ("CS") has been correlated with increased methionine biosynthesis. See e.g. Thompson, et al., "Methionine Biosynthesis in Lemna," *Plant Physiol.*; Vol. 69; pp. 1077–1083; (1982); incorporated herein by reference.

CS catalyses the first step of methionine biosynthesis (see FIG. 1). The apparent physiological substrate is O-phosphohomoserine, and thus CS competes for this substrate with threonine synthase, an enzyme involved in threonine biosynthesis. CS levels are inversely correlated with methionine levels, indicating regulation by methionine or related compounds. Over-expression of CS should lead to increased flux through CS, allowing for increased methionine biosynthesis.

For increased threonine synthesis, methionine adenosyl-transferase ("MAT"), can be over-expressed. The direct product of MAT, S-adenosylmethionine ("SAM") has been demonstrated to strongly activate threonine synthase ("TS") in vitro. Increasing the expression of MAT leads to increased synthesis of SAM, which allows a greater concentration of TS to be in active form. Increased TS activity leads to an increase in threonine biosynthesis. Because of the co-expression of the sink protein, as contemplated by the subject invention, the levels of free threonine will not be sufficiently high during target protein synthesis to negatively affect aspartate kinase-homoserine dehydrogenase activity or to promote catabolic activities.

For increased lysine synthesis, over-expression of dihydrodipicolinate synthase ("DHPS") is effective. A substrate of DHPS, aspartic semialdehyde, is a branchpoint intermediate, being a precursor to homoserine biosynthesis and to DHP biosynthesis. An increase in DHPS activity allows for greater conversion toward DHP biosynthesis and, thus, lysine biosynthesis. Co-expression of a sink protein should cause the levels of free lysine to be sufficiently low during target protein synthesis such that DHPS or AK-HSD activity is not negatively affected.

Under-expression of a Gene Coding for a Target Enzyme

A decrease in the concentration of a target enzyme is achieved, for example by the use of an antisense construct. See e.g. Temple, S. J., et al., "Modulation of Glutamine Synthetase Gene Expression in Tobacco by the Introduction of an Alfalfa Glutamine Synthetase Gene in Sense and Antisense Orientation: Molecular and Biochemical Analysis." *Molecular and General Genetics*, Vol. 238(2–3); pp. 315–325; (1993); incorporated herein by reference. Expression of an antisense gene construct leads to a decrease in translatable MRNA for enzyme synthesis, thereby leading to a decrease in target enzyme concentration and metabolic flow at the target enzyme.

For example, threonine synthase ("TS") catalyzes the first committed step of threonine biosynthesis. The physiological substrate for TS is O-phosphohomoserine and thus TS competes for this substrate with CS. Under-expression of TS reduces the flux through TS, and thus provides additional substrate (O-phosphohomoserine) for CS, thereby increasing metabolic flow toward methionine biosynthesis. Furthermore, decreased levels of TS lead to a decrease in threonine biosynthesis and concentration, which in turn reduce the level of feedback inhibition by this metabolite on AK-HSD, again resulting in increased methionine biosynthesis. Thus, carbon and metabolic energy are directed away from threonine biosynthesis towards methionine biosynthesis.

For threonine, under-expression of DHPS and CS, is effective for the same reasons as previously discussed. For example, reduced levels of CS allow for increased availability of O-phosphohomoserine for TS, thereby increasing threonine biosynthesis.

Furthermore, a reduction in the levels of TS decrease threonine biosynthesis and inhibition of AK-HSD activity by threonine because free threonine levels are relatively low. These actions increase lysine (and methionine) biosynthesis. Because MAT has a strong positive influence on TS activity, a suppression of its synthesis decreases the level of active TS and the effect is similar to under-expression of TS.

Generation of an Alternative Metabolic Branchpoint

It is sometimes desirable to redirect metabolic flow away from a major branchpoint where one metabolite is shared among several competing pathways to a more direct route or to the production of a new metabolite. This can be done by expressing a single gene coding for the target enzyme or may involve the expression of multiple genes coding for multiple enzymes. See e.g. Tarczynski, M. C., et al., "Expression of a Bacterial mtlD Gene in Transgenic Tobacco Leads to Production and Accumulation of Mannitol," *Proc. Natl. Acad. Sci. USA*; Vol. 89; pp. 2600–2604; (1992); incorporated herein by reference.

For example, O-phosphohomoserine is the primary if not exclusive physiological substrate for CS in higher plants. The first committed enzymes in methionine biosynthesis (CS) and threonine biosynthesis (TS) compete for O-phosphohomoserine. To increase methionine biosynthesis, homoserine can be diverted, in part, towards malonylhomoserine by the expression of a gene encoding homoserine malonyltransferase. Malonylhomoserine, in addition to O-phosphohomoserine, is a substrate for CS but not for TS, and thus increased levels of substrate should be available for CS, leading to an increase in methionine biosynthesis.

Alteration of Biochemical Properties of a Target Enzyme

Modification of the gene that codes for the target enzyme are made according to this approach, altering the biochemical characteristics of the enzyme. See e.g. U.S. Pat. No. 5,367,110, issued Nov. 22, 1994 to Galili, et al., incorporated herein by reference. Several known methods exist to alter biochemical properties of enzymes. These methods include site directed mutagenesis. See e.g. Deng, et al., "Site-Directed Mutagenesis of Virtually any Plasmid by Eliminating a Unique Site," *Anal. Biochem.*; Vol. 200; pp. 81–88; (1992); incorporated herein by reference. Depending on the result of the alteration, metabolic flux may be increased or decreased through the target enzyme. See e.g. Shaul, et al., "Threonine Overproduction in Transgenic Tobacco Plants Expressing a Mutant Desensitized Aspartate Kinase of *Escherichia coli,*" *Plant Phys.*; Vol. 100; pp. 1157–1163; (1992); and Brzovic, et al., "Substitution of Glutamic Acid 109 by Aspartic Acid Alters the Substrate Specificity and Catalytic Activity of the Beta-subunit in the Tryptophan Synthase Bienzyme Complex from Salmonella Typhimurium," *Biochemistry*; Vol. 31; pp. 1180–90; (1992); both incorporated herein by reference.

AK-HSD catalyzes the first step in the biosynthesis of the aspartate family of amino acids. This enzyme is normally feedback regulated by lysine and threonine. Mutant forms of AK-HSD have been selected both in *E. coli* and in plants, these organisms have been shown to over-produce free threonine, and methionine, lysine and isoleucine. There is little or no change in bound threonine, methionine, lysine or isoleucine contents. See e.g. Galili et al., cited hereinabove.

Over-expression of a Preselected Gene

The present invention further involves genetically modifying a plant seed to preferentially express a preselected protein. Examples include, but are not limited to, a methionine-rich protein, a cysteine-rich protein, a lysine-rich protein, a glycine-rich protein, a tryptophan-rich protein, and a tyrosine-rich protein.

As used herein, "rich" means containing a higher percentage of amino acid than the average protein.

As used herein, "promoter" refers to a DNA sequence in a gene, usually upstream (5') to its coding sequence, which controls the expression of the coding sequence by providing the recognition for RNA polymerase and other factors required for promoter transcription. Preferred promoters are those that allow expression of the preselected protein specifically in seeds to avoid any potential deleterious effect in non-seed organs. Such promoters will be well known to a person skilled in the art.

Examples of seed-specific promoters include, but are not limited to, the promoters of seed storage proteins which express these proteins in seeds in a highly regulated manner. Thompson, et al., *BioEssays*; Vol. 10; pp. 108–113; (1989); incorporated herein in its entirety by reference. Several seed specific promoters for expression of proteins in seeds of dicotyledonous plants that will be of particular use include bean β-phaseolin, napin, β-conglycinin, and soybean lectin. For monocotyledonous plants, maize 15 kD zein, 22 kD zein, γ-zein, waxy, shrunken 1, globulin 1, and shrunken 2 promoters will be particularly useful to produce expression of peptides. Those skilled in the art will recognize other promoters as well that will provide constructs for increased levels of the preselected protein in the plant chosen for transformation.

In a highly preferred embodiment, the preselected protein is a methionine rich 2S seed storage protein such as Brazil nut protein (BNP). Altenbach, et al., *Plant Mol. Biol.*; Vol. 8; pp. 239–250; (1987); incorporated herein in its entirety by reference. A natural or constructed DNA or RNA sequence encoding this protein is introduced into plant cells by any method of transformation that stably incorporates the gene into the plant genome. This can include a variety of vectors, such as viral vectors, episomal vectors, shuttle vectors, Ti plasmid vectors and the like, all in accordance with well known procedures. Sun, et al., *Eur. Patent Appl.* EP No. 295,959; (1991); incorporated herein in its entirety by reference.

A "vector" is a replicon, such as a plasmid, cosmid, or bacteriophage, to which another DNA segment may be attached so as to bring about replication of the attached segment, or to allow its introduction into a cellular host.

As used herein with respect to a protein, the term "heterologous" means that the gene or gene fragment encoding the protein is obtained from one or more sources other than the genome of the species of plant within which it is ultimately expressed. The source can be natural, e.g., the gene can be obtained from another source of living matter, such as bacteria, yeast, fungi and the like, or a different species of plant. The source can also be synthetic, e.g., the gene or gene fragment can be prepared in vitro by chemical synthesis.

As used herein with respect to a preselected protein, the term "expresses" means that the gene encoding this protein is stably incorporated into the genome of the cells, so that the product encoded by the gene, e.g., a methionine-rich protein such as Brazil nut protein (BNP), is produced within the cells. For example, novel plants resulting from expression of BNP, contain extractable seed BNP levels of 0.5%, and preferably, at least 2%.

The properties of the nucleic acid sequences encoding the preselected protein may be varied and the preferred embodiment describes a number of features which may be advantageous but that a person skilled in the art will recognize as not being absolutely essential. These include the selection of a particular construct and vector to introduce the sequence into the cell and produce expression of the protein. A skilled artisan can construct an expression cassette adequate for expression of the preselected protein in the chosen cellular system with no undue experimentation. The heart of the invention is the level of the preselected protein; therefore, additional copies of the nucleic acid sequence will normally result in increased inhibition of synthesis of the endogenous protein.

By way of example, and not limitation, those skilled in the art will readily appreciate that additional proteins, such as 10 kDa zein and 2S albumin from alfalfa may be substituted for the BNP protein as the preselected seed protein. See e.g. *Mol. Gen. Genet.* (1988) Vol. 211, pp. 477–484; and *J. Exp. Bot.*, Vol. 41, 233 pp. 1541–7, 1990, respectively; both incorporated herein in their entirety by reference. The skilled artisan will recognize that choice Of the preselected protein will be based on the amino acid composition of the protein and its ability to accumulate in seeds. This includes all classes of seed storage proteins; the 2S, 7S, and 11S proteins with or without modification to increase the content of the designated amino acid in the protein. The amino acid can be chosen for its nutritional value to produce a value-added trait to the plant as well as its purpose as a sink to limit availability to the designated endogenous protein. Examples of suitable sources for protein sequences usable in accordance with the present invention are plants, in particular higher plants. Amino acids desirable for value-added traits as well as a source to limit synthesis of an endogenous protein include, but are not limited to methionine, cysteine, glycine, lysine, tryptophan, and tyrosine.

As used herein, "plant" refers to either a whole plant, a plant part, a plant cell, or a group of plant cells. The class of plants which can be used in the method of the invention is generally as broad as the class of seed-bearing higher plants amenable to transformation techniques, including both monocotyledonous and dicotyledonous plants. The transformation of the plants in accordance with the invention may be carried out in essentially any of the various ways known to those skilled in the art of plant molecular biology. These include but are not limited to particle bombardment, microinjection, electroporation, and Agrobacterium-mediated DNA transfer.

Following transformation, regeneration will normally be involved in obtaining a whole plant from the transformation process. Techniques for regenerating plants from tissue culture, such as transformed protoplasts or callus cell lines, are known in the art. See, e.g., Phillips, et al., *Plant Cell Tissue Organ* Culture; Vol. 1; p. 123; (1981); Patterson, K E. and N. P. Everett, *Plant Sci.*; Vol. 42; pp. 125–132; (1985); Wright, et al., *Plant Cell Reports*; Vol. 6; pp. 83–89; (1987); Barwale, et al., *Planta*; Vol. 167; p. 473; (1986); all incorporated herein in their entirety by reference. The selection of an appropriate method is within the skill of the art.

Examples of the practice of the present invention detailed herein relate specifically to soybean plants and expression vectors operable in dicots. Soybean was chosen as a model system for these examples primarily because of the present capability to regenerate soybean plants from transformed individual soybean cells in a manner now known in the art. The expression vectors utilized herein are demonstrably capable of operation in cells of many dicotyledonous plants both in tissue culture and in whole plants. The invention disclosed herein is thus operable in dicotyledonous species to transform individual plant cells and to achieve full, intact plants in dicot plant species which can be regenerated from transformed plant calli and which express preselected seed proteins. For those species not presently regenerable, the present invention is fully operable when the techniques for such regeneration become developed.

In addition, chimeric expression vectors involving seed proteins are also known and have been described in the literature which have been demonstrated to be operable in cells of monocots, at least in tissue culture. It is reasonable then to expect that these vectors will also be operable in whole monocot plants when the techniques for regenerating these plants are perfected so that any preselected seed protein can be expressed in any monocotyledonous plant seed. The present invention is thus applicable to monocots as well as to dicots.

Therefore, practice of this invention can be used to improve crop plants like rice, maize, wheat, and barley with few modifications. An example of such an embodiment would be the introduction of a high lysine derivative of α-hordothionin into a barley or wheat cell to reduce the purothionin content of the seed and increase its lysine content.

Thionins are small antimicrobial proteins present in the endosperm of barley, wheat, and other plant species.

Florack, et al., *Plant Mol. Biol.*; Vol. 24; pp. 83–96; (1994); incorporated herein in its entirety by reference. Native α-hordothionin is rich in arginine and lysine residues, containing five residues (10%) of each. Several derivatives of this protein have been made in which other amino acids were replaced with lysine to produce a compound less toxic to fungi and significantly more enriched with lysine (29% lysine).

Purothionins are also small, lysine-rich proteins in the endosperm of wheat and several other species of Gramineae. Wada, K. *Plant & Cell Physiol* 23(8), 1357–1361; (1982); incorporated herein in its entirety by reference. Purothionins are lethal to brewer's yeast and, as a result, barley or wheat with high levels of these proteins cannot be used for making high quality beers.

However, according to this invention, a high-lysine α-hordothionin or another genetically-engineered thionin designed for lysine enrichment and reduced toxicity to microorganisms could be used to decrease the levels of purothionins and increase the lysine content of barley, wheat, or other graminaceous plants. The lysine-enriched residue could be sold for feed following the brewing process.

The foregoing is one description of the scope of the invention and a skilled artisan will recognize many other examples of plant improvement to which the invention can be applied.

The present invention can be better understood by reference to the following more detailed example which illustrates its various applications, but is in no way intended to limit the scope thereof.

EXPERIMENTAL

Alteration of Amino Acid Pathway

In order to achieve seed-specific expression of the AK gene and target the enzyme to the plastid, the procedure is used as described in Karchi, et al., "Seed-specific Expression of a Bacterial Desensitized Aspartate Kinase Increases the Production of Seed Threonine and Methionine in Transgenic Tobacco," *The Plant Journal*; Vol. 3(5); pp. 721–727; (1993); incorporated herein in its entirety by reference. The phaseolin construct is used.

TRANSFORMATION OF GLYCINE MAX WITH A METHIONINE-RICH SEED STORAGE PROTEIN

Plant Transformation

Soybean (*Glycine max*) seed, Pioneer variety 9341, was surface sterilized by exposure to chlorine gas evolved in a glass bell jar. Gas was produced by adding 3.5 ml hydrochloric acid (34–37% w/w) to 100 ml sodium hypochlorite (5.25% w/w). Exposure was for 16–20 hours in a container approximately one cubic foot in volume. Surface sterilized seed was stored in petri dishes at room temperature. Seed was germinated by plating on $\frac{1}{10}$ strength agar solidified medium according to Gamborg [B5 basal medium with minimal organics, Sigma Chemical Co., cat. no. G5893, 0.32 gm/L; sucrose, 0.2% w/v and 2-[Nmorpholino] ethanesulfonic acid (MES), 3.0 mM] without plant growth regulators and culturing at 28° C. with a 16 hour day length and cool white fluorescent illumination of approximately 20 mEm2Sl. After three or four days, seed could be prepared for cocultivation. The seed coat was removed and the elongating radical was removed 3–4 mm below the cotyledons. Ten prepared seeds were held in each of several petri dishes.

Construction of Plasmids

For construction of the plasmid pl2GUSBN17, containing one copy of the chimeric methionine-rich protein gene (BNP), the plasmid pARC12 (Prosen D. E. and R. B. Simpson, *Biotechnology Vol.* 5, pp. 966–971; (1987); incorporated herein in its entirety) was used. This is a 29.5 kb plasmid which is part of a binary vector system of Agrobacterium and contains the chimeric gene nopaline synthase/neomycin phosphotransferase II as a selectable marker for plant cells. The chimeric gene, CaMV35S/βglucuronidase, obtained from the plasmid pBl221 (Jefferson, R. A., *Plant Mol. Bio. Reporter*; Vol. 5(4), pp. 387–405; (1987); incorporated herein in its entirety by reference) was inserted into PARC12, resulting in plasmid pl2GUS-15. The plasmid pD3-8-12 (Altenbach, et al., *Plant Mol. Biol.*; Vol. 13; pp. 513–522; (1989); incorporated herein in its entirety by reference), contains the BNP gene in the vector pTZ19U. The pD3-8-12 plasmid was cleaved with Hind III and inserted into the Hind III site of plasmid pl2GUS-15. The resulting plasmid pl2GUSBN17 is about 36 kb in size, contains one copy of the BNP gene, and confers resistance to ampicillin and tetracycline to the bacterial host.

For the construction of a plasmid containing four copies of the methionine-rich protein gene, the plasmid pD3-8-12 was used as the starting point. The BNP gene was excised from pD3-8-12 by digestion with Eco R1, Hind III, and Xmn 1. The ends of the fragment were made blunt with the Kenow fragment of DNA polymerase, and a 3 kb fragment containing the chimeric gene was gel-purified. This fragment was ligated to the plasmid pD3-8-12 which had been digested with Sma 1 and treated with calf intestinal phophatase. The resulting plasmid, called pD3-8-12-2X, contained two copies of the chimeric methionine-rich BNP gene in tandem array.

To produce the plasmid containing four copies of the chimeric gene, the pD3-8-12-2X plasmid was digested with Eco R1 and Hind III and the ends were made blunt with the Klenow fragment of DNA polymerase. A 6 kb fragment containing two copies of the chimeric gene was isolated. This fragment was ligated to the plasmid pD3-8-12-2X which had been digested with Sma I and treated with calf intestinal phosphatase. The resulting plasmid is pD3-8-12-4X.

The chimeric BNP genes were then inserted into the Ti plasmid vector pARC12. A 12 kb fragment from pD3-8-12-4X was excised by digestion with Eco R1 and Hind III and ligated to pARC12 which had been digested with Eco R1 and Hind III. The resulting plasmid, pl2-4X, contains four copies of the BNP gene between the tDNA borders, as well as a chimeric nopaline synthase neomycin phosphotransferase II gene for selection in plant cells. The plasmid was then transferred from *E. coli* to *Agrobacterium tumefaciens* strain LBA 4404 by triparental mating. The identities of the resulting bacteria were confirmed by southern blot analysis.

Preparation of Agrobacterium Tumefaciens LBA4404/pl2GUSBN17 and pl2-4X

Overnight cultures of *Agrobacterium tumefaciens* strain LBA 4404 harboring the binary plasmid pl2GUSBN17 (DP1816, one copy BNP sequence) or pl2-4X (DP1813, four copies BNP sequence), grown to log phase in Minimal A medium containing tetracycline, 1.0 mg/ml, were pooled and an optical density measurement at 550 nm was taken. Sufficient volume of the culture was placed in 15 ml conical centrifuge tubes such that upon sedimentation between 1.0 and 2.0×1010 cells were collected in each tube, where O.D.550 1.0=1.4×109 cells/ml. Sedimentation was by centrifugation at 6000 g for 10 minutes. After centrifugation the supernatant was decanted and the tubes were held at room temperature until inoculum was needed but not longer than one hour.

Transformation

Inoculations were conducted in batches such that each plate of seed was treated with a newly resuspended pellet of Agrobacterium. One at a time the pellets were resuspended in 20 ml inoculation medium. Inoculation medium consisted of B5 salts (G5893), 3.2 gm/L; sucrose, 2.0% w/v. 6-benzylaminopurine (BAP), 44 mM; indolebutyric acid (IBA), 0.5 mM; acetosyringone (AS), 100 mM and was buffered to pH 5.5 with MES, 10 mM. Resuspension was by vortexing. The inoculum was then poured into a petri dish containing prepared seed and the cotyledonary nodes were macerated with a surgical blade. This was accomplished by dividing seed in half by longitudinal section through the shoot apex preserving the two whole cotyledons. The two halves of the shoot apex were then broken off their respective cotyledons by prying them away with a surgical blade. The cotyledonary node was then macerated with the surgical blade by repeated scoring along the axis of symmetry. Care was taken not to cut entirely through the explant to the abaxial side. Twenty explants were prepared in roughly five minutes and then incubated for 30 minutes at room temperature without agitation. Additional plates were prepared during this time. After 30 minutes the explants were transferred to plates of the same medium solidified with Gelrite (Merck & Co., Inc.), 0.2%. w/v. Explants were embedded with the adaxial side up and level with the surface of the medium and cultured at 22° C. for three days under cool white fluorescent light, approximately 20 $mEm^2S^l$.

Culture and Selection

After three days the explants were moved to liquid counterselection medium. Counterselection medium consisted of B5 salts (G5893), 3.2 gm/L; sucrose, 2.0% w/v; BAP, 5.0 mM; IBA 0.5 mM; vancomycin, 200 mg/ml; cefotaxime, 500 mg/ml and was buffered to pH 5.7 with MES, 3 mM. Ten explants were washed in each petri dish with constant, slow gyratory agitation at room temperature for four days. Counterselection medium was replaced four times.

The explants were then picked to agarose solidified selection medium. Selection medium consisted of B5 salts (G5893), 3.2 gm/L; sucrose, 2.0%, w/v; BAP, 5.0 mM; IBA, 0.5 mM; kanamycin sulfate, 50 mg/ml; vancomycin, 100 mg/ml; cefotaxime, 30 mg/ml; timentin, 30 mg/ml and was buffered to pH 5.7 with MES, 3.0 mM. Selection medium was solidified with SeaKem agarose, 0.3% w/v. The explants were embedded in the medium, adaxial side down and cultured at 28° C. with a 16 hour day length and cool white fluorescent illumination of 60–80 $mEm^2S^l$.

After two weeks explants were again washed with liquid medium on the gyrotory shaker. This time the wash was conducted overnight in counterselection medium containing kanamycin sulfate, 50 mg/ml. The following day explants were picked to agarose solidified selection medium. Again they were embedded in the medium, adaxial side down, Culture was as before for another two week period.

Regeneration

After one month on selective media transformed tissue became visible as green sectors of regenerating tissue against a background of bleached, less healthy tissue. Explants without green sectors were discarded, explants with green sectors were transferred to elongation medium. Elongation medium consisted of B5 salts (G5893), 3.2 gm/L; sucrose, 2.0% w/v; IBA, 3.3 mM; gibberellic acid, 1.7 mM; vancomycin, 100 mg/ml; cefotaxine, 30 mg/ml; and timentin, 30 mg/ml, buffered to pH 5.7 with MES, 3.0 mM. Elongation medium was solidified with gelrite, 0.2% w/v. They were embedded adaxial side up and cultured as before. Culture was continued on this medium with transfers to fresh plates every two weeks. When shoots became 0.5 cm in length they were excised at the base and placed in rooting medium in 13×100 mm test tubes. Rooting medium consisted of B5 salts (G5893), 3.2 gm/L; sucrose, 15 gm/L; nicotinic acid, 20 mM; pyroglutamic acid (PGA), 900 mg/L and IBA, 10 mM. It was buffered to pH 5.7 with MES, 3.0 mM and solidified with Gelrite, 0.2% w/v. After ten days the shoots were transferred to the same medium without IBA or PGA. Shoots were rooted and held in these tubes under the same environmental conditions as before.

When a root system was well established the plantlet was transferred to sterile soil mix in plant cons (ICN Biomedicals, Inc., cat. no. 26-720 & 1-02). Temperature, photoperiod and light intensity remained the same as before. Under these conditions the regenerants became vigorous, mostly normal (though small) plants. When their root systems again became well established a corner of the plant con was cut off and the plants were gradually hardened off in an environmental chamber or greenhouse. Finally they were potted in soil mix and grown to maturity, bearing seed, in a greenhouse.

Growth, Increase, and Harvest of Transgenic Soybeans

Seed from untransformed and transformed plants of the same variety (9341) was planted in the spring of 1992 and harvested in the fall of 1992 in Iowa. Each individual line was kept separate while grown in one or more 10.5 foot rows for maximum increase. Lines from transformation events wherein one copy of the BNP gene was inserted are referred to as BNP1X. Lines in which four copies were inserted are designated BNP4X.

Most of the harvested BNP4X seed in the fall of 1992 was increased in Puerto Rico. This seed was planted by line in December, 1992 and harvested by line in March, 1993.

Part of the increased, harvested seed was returned for yield test and further laboratory testing. The rest was replanted by line in March, 1993 and harvested by line in June, 1993 in Puerto Rico. The entire second cycle increase was about 2 acres, or a little more than 0.1 A per line.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Variations on the above embodiments are within the ability of one of ordinary skill in the art, and such variations do not depart from the scope of the present invention as described in the following claims.

What claimed is:

1. A method for increasing the level of a target amino acid in seed of a plant comprising stably transforming the plant (1) to manipulate a metabolic pathway of the amino acid to provide an additional source of the amino acid and (2) and concomitantly providing a complementary sink protein, such that there is an increase in the level of the amino acid compared to a plant which has not been transformed, wherein the amino acid is lysine, methionine or threonine.

2. A method for increasing the level of a target amino acid in seed of a plant comprising stably transforming the plant (1) to manipulate a metabolic pathway of the amino acid to provide an additional source of the amino acid and (2) and concomitantly providing a complementary sink protein, such that there is an increase in the level of the amino acid compared to a plant which has not been transformed, wherein the amino acid is lysine, methionine or threonine and wherein the plant is selected from the group consisting of soybeans, corn, canola, sunflower, wheat, barley, oats, millet, rice, sorghum and rye.

3. The method of claim 1 wherein the target amino acid is selected from the group consisting of lysine, methionine and threonine.

4. The method of claim 3 wherein the metabolic pathway is manipulated by over-expression of key enzymes, under-expression of key enzymes, metabolic branchpoint generation or alteration of enzyme biochemical properties.

5. The method of claim 4 wherein the seed is selected from the group consisting of soybeans, canola, corn, sunflower, wheat, barley, oats, millet, rice, sorghum and rye.

6. The method of claim 5 wherein the metabolic pathway is manipulated by over-expression of key enzymes, under-expression of key enzymes or alteration of enzyme biochemical properties.

7. The method of claim 6 wherein the seed is selected from the group consisting of soybean, corn, sorghum, canola and sunflower.

8. The method of claim 7 wherein the seed is selected from the group consisting of soybean, corn and canola.

9. The method of claim 8 wherein the seed is selected from the group consisting of soybean seed.

10. The method of claim 8 wherein the metabolic pathway is manipulated by alteration of enzyme biochemical properties.

11. The method of claim 7 wherein the level of methionine is increased in the seed by
   a) over-expressing a gene coding for Brazil nut protein; and
   b) over-expression of a key enzyme, under-expression of a key enzyme or alteration of enzyme biochemical properties.

12. The method of claim 11 wherein the level of methionine is increased in the seed by alteration of enzyme biochemical properties.

13. The seed of claim 12 wherein the metabolic pathway is manipulated by over-expression of key enzymes, under-expression of key enzymes, metabolic branchpoint generation or alternation of enzyme biochemical properties.

14. The seed of claim 13 wherein the seed is selected from the group consisting of soybeans, canola, corn, sunflower, wheat, barley, oats, millet, rice, sorghum and rye.

15. The seed of claim 14 wherein the seed is selected from the group consisting of soybean, corn, sorghum, canola and sunflower.

16. The seed of claim 15 wherein the seed is selected from the group consisting of soybean, corn and canola.

17. The seed of claim 16 wherein the seed is soybean.

18. The seed of claim 17 wherein the level of methionine is increased in the seed by
   a) over-expressing a gene coding for Brazil nut protein; and
   b) over-expression of key enzymes, under-expression of key enzymes or alteration of enzyme biochemical properties.

19. The seed of claim 18 wherein the metabolic pathway is manipulated by alteration of enzyme biochemical properties.

20. The method of claim 1 wherein a rate-limiting enzyme is over-expressed.

21. The method of claim 20 wherein the enzyme is cystathionine gamma-synthase, methionine adenosyltransferase, and/or dihydrodipicolinate synthase.

22. The method of claim 1 wherein a gene coding a target enzyme is under-expressed.

23. The method of claim 22 wherein the enzyme is threonine synthase, cystathionine gamma-synthase, dihydrodipicolinate synthase and/or methionine adenosyltransferase.

24. The method of claim 1 wherein a metabolite common to several competing pathways is redirected to a more direct route or to the production of a new metabolite.

25. The method according to claim 24 wherein homoserine malonyltransferase is expressed.

26. The method of claim 1 wherein biochemical properties of a target enzyme are altered.

27. The method of claim 26 wherein the enzyme is aspartate kinase and/or tryptophan synthase.

28. The method of claim 1 wherein the protein is a seed storage protein, $\alpha$-hordothionin or a derivative thereof.

29. A plant seed prepared by the method of claim 1.

30. A plant seed prepared by the method of claim 3.

31. The method of claim 2 wherein the metabolic pathway is manipulated by over-expression of key enzymes, under-expression of key enzymes, metabolic branchpoint generation or alteration of enzyme biochemical properties.

32. A plant seed prepared by the method of claim 2.

* * * * *